United States Patent

Haase et al.

[11] Patent Number: 6,057,444
[45] Date of Patent: May 2, 2000

[54] PROCESS FOR THE PREPARATION OF PHENYLDICHLORO-1,3,5-TRIAZINE COMPOUNDS

[75] Inventors: Jürg Haase, Bettingen, Switzerland; Tanja Mössner, Neuenburg, Germany

[73] Assignee: Ciba Specialty Chemicals Corporation, Tarrytown, N.Y.

[21] Appl. No.: 09/251,809

[22] Filed: Feb. 17, 1999

[30] Foreign Application Priority Data

Feb. 20, 1998 [CH] Switzerland .............................. 407/98

[51] Int. Cl.$^7$ ........................ C07D 251/10; C07D 251/12
[52] U.S. Cl. .......................... 544/217; 544/219; 544/223
[58] Field of Search ................................... 544/217, 219, 544/223

[56] References Cited

U.S. PATENT DOCUMENTS

| | | | |
|---|---|---|---|
| 2,691,018 | 10/1954 | Joyce et al. ............................ | 260/248 |
| 2,691,019 | 10/1954 | Munro et al. .......................... | 260/248 |
| 2,691,020 | 10/1954 | Gadea et al. ........................... | 260/249 |
| 3,907,721 | 9/1975 | Gurgiolo .................................. | 260/2.5 |
| 4,092,466 | 5/1978 | Fletcher et al. ......................... | 526/13 |

FOREIGN PATENT DOCUMENTS 634399   1/1964   Belgium .

OTHER PUBLICATIONS

Paquette, Enclopedia of Reagents for Organic Synthesis vol. 3 2045–2047, 1995.

Paquette, Enclopedia of Reagents for Organic Synthesis vol. 7, 2045–2047, 1995.

Beilst. E III/IV 26, S. 582–583.

(List continued on next page.)

*Primary Examiner*—John M. Ford
*Assistant Examiner*—V Balasubramanian
*Attorney, Agent, or Firm*—Kevin T. Mansfield

[57] ABSTRACT

A process is described for the preparation of an aryl-1,3-5-triazine compound of formula (1). This process comprises reacting an aldehyde compound of formula (2) with biuret, compound of formula (3), in hydrochloric medium or with methyl sulfate ($1^{st}$ reaction step), then oxidizing the resulting compound of formula (4) to the compound of formula (5) or (6) ($2^{nd}$ reaction step) and subsequently chlorinating the compound so obtained to the compound of formula (1) ($3^{rd}$ reaction step) according to the following scheme:

1st step:

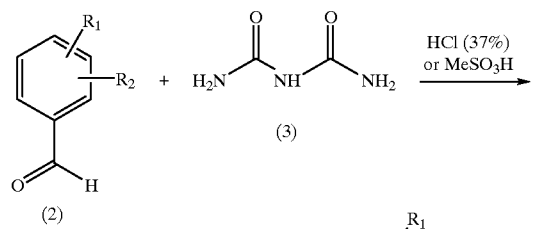

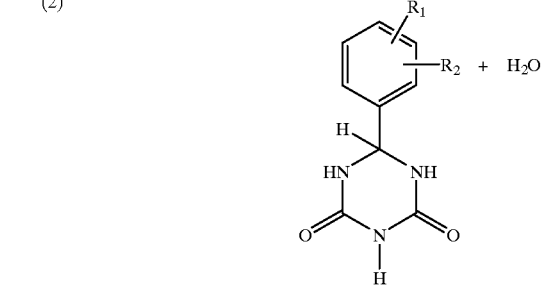

2nd step:

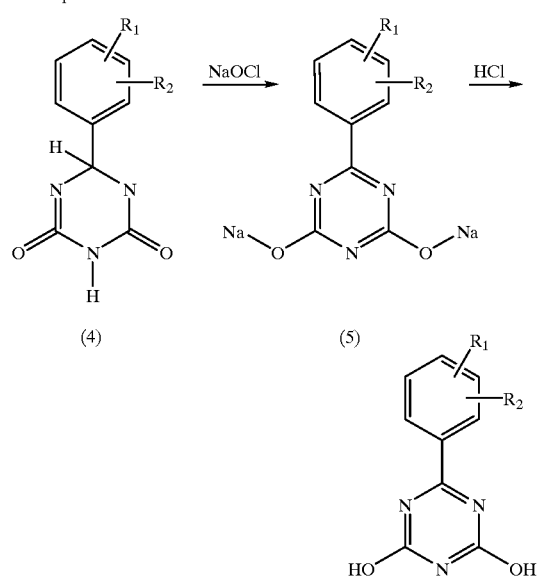

3rd step:

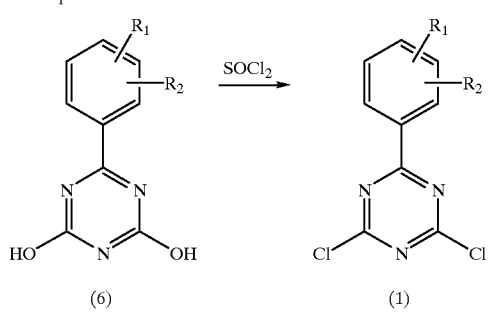

In the above scheme:

$R_1$ and $R_2$ are each independently of the other hydrogen; hydroxy or $C_1$–$C_5$alkoxy. The compounds of formula (1) are used as UV absorbers or as starting products for the preparation of UV absorbers.

6 Claims, No Drawings

OTHER PUBLICATIONS

Butler et al., J. Chem. Research (S), (1994), 3, XP–002104418.

Smolin; Rapaport: "s–Triazines and Derivatives", Interscience Publishers Inc., NY, p. 26, XP–002104421.

Nigam et al., Agra University Journal of Research, vol. VII, No. 1, (1958), pp. 67–75, XP–002104420.

Étienne et al., Bull. Soc. Chim. Fr., (1975), No. 5–6, pp. 1419–1424, XP–002104419.

Chem. Abstr. 84:31009y for Bull. Soc. Chim. Fr., (1975), No. 5–6, pp. 1419–1424.

PROCESS FOR THE PREPARATION OF PHENYLDICHLORO-1,3,5-TRIAZINE COMPOUNDS

The present invention relates to a simple three-stage process for the preparation of phenyldichloro-1,3,5-triazine compounds, starting from biuret and from a benzaldehyde compound.

Phenyldichlorotriazines and their methoxy and hydroxy derivatives can be obtained, for example, by benzoylation of dicyandiamide, conversion of the benzoyldicyandiamide into benzoylbiuret, cyclisation of this compound to phenyldihydroxytriazine and subsequent chlorination with $PCl_4$ according to the following scheme:

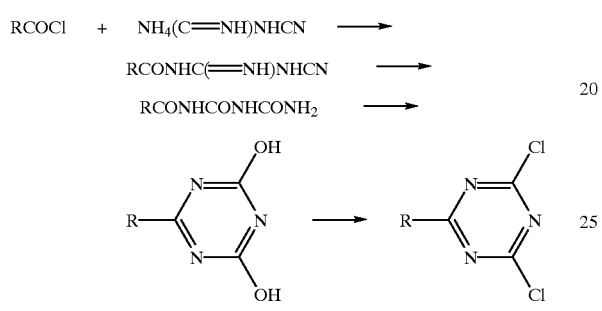

(R=phenyl; alkoxyphenyl; hydroxyphenyl).

This method of preparation is known, for example, from U.S. Pat. No. 2,691,020.

Phenyldihydrotriazine (compound of formula (4), $R_1$, $R_2$=hydrogen) which is unsubstituted in the phenyl ring can be prepared by reacting biuret with benzaldehyde in concentrated suplfuric acid. This reaction is described, inter alia, in Beilst. E III/IV 26, p. 582–583. The analogous preparation of the corresponding hydroxy- or alkoxy-substituted phenyldihydrotriazines is not successful with this process.

Surprisingly, it has now been found that these compounds can be obtained by condensing biuret with a substituted phenylaldehyde to dioxydihydrotriazines in hydrochloric medium or in the presence of methyl sulfate.

The novel process for the preparation of an aryl-1,3-5-triazine compound of formula (1) comprises reacting an aldehyde compound of formula (2) with biuret, compound of formula (3), in hydrochloric medium or with methanesulfonic acid ($1^{st}$ reaction step), then oxidising the resulting compound of formula (4) to the compound of formula (5) or (6) ($2^{nd}$ reaction step) and subsequently chlorinating the compound so obtained to the compound of formula (1) ($3^{rd}$ reaction step) according to the following scheme:

1st step:

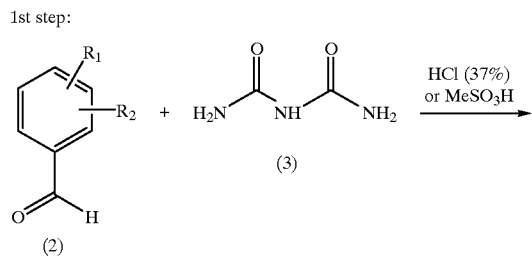

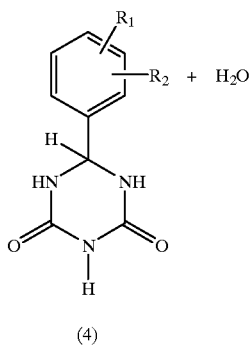

2nd step:

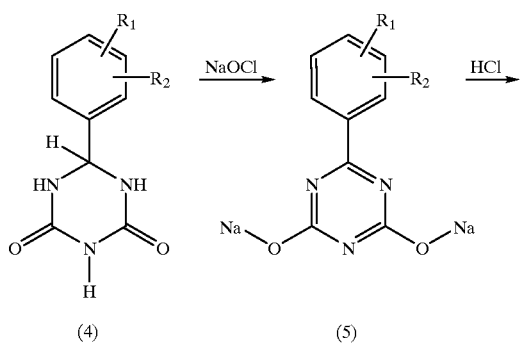

3rd step:

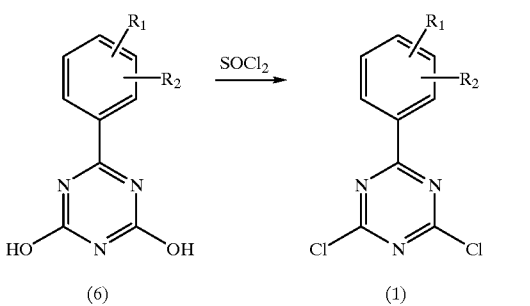

In the above scheme:

$R_1$ and $R_2$ are each independently of the other hydrogen; hydroxy or $C_1$–$C_5$alkoxy.

$C_1$–$C_5$Alkoxy is straight-chain or branched alkoxy radicals, such as methoxy, ethoxy, propoxy, butoxy or pentyloxy.

The novel process preferably relates to the preparation of compounds of formula (1), wherein $R_1$ is $C_1$–$C_5$alkoxy; and $R_2$ is hydrogen, very particularly preferably of compounds of formula (1), wherein $R_1$ is methoxy.

The reaction time for the first reaction step is usually from 1 to 24 hours, preferably from 5 to 12 hours. The reaction is carried out at a temperature in the range from 0 to 60° C., preferably at room temperature.

The first reaction step is usually carried out by placing first the hydrochloric acid or MeSO$_3$H in a vessel and then stirring in about 1 mol of biuret and adding 1 mol of the compound of formula (2). Subsequently, about 0.2 mol of biuret and hydrochloric acid or MeSO$_3$H are added and the reaction mixture is stirred for about 1 to 8 hours.

Solvents and other additives are generally not necessary for the first reaction step. If required, it is possible to add monovalent alcohols as solvent, for example methanol, ethanol or i-propanol. The use of catalysts may also be forgone.

In the second reaction step, the compound of formula (4) is oxidised in aqueous suspension with NaOCl to the compound of formula (6). The reaction mixture is charged with HCl. The released cyanuric acid (compound of formula (6)) is isolated and dried.

In the third reaction step, the compound obtained is chlorinated with thionyl chloride in the presence of DMF to the compound of formula (1).

The compounds of formula

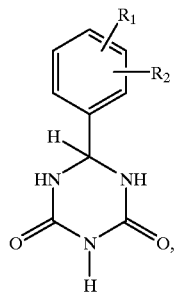

(4)

wherein

R$_1$ and R$_2$ are each independently of the other hydrogen; hydroxy or C$_1$–C$_5$alkoxy;

where R$_1$ and R$_2$ are not simultaneously hydrogen;

are novel compounds and are another subject matter of this invention.

The compounds of formula (4) can be prepared by condensing biuret with an aldehyde to dioxydihydrotriazine in hydrochloric medium or in the presence of methanesulfonic acid according to the following reaction scheme:

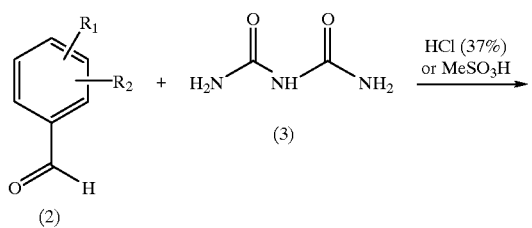

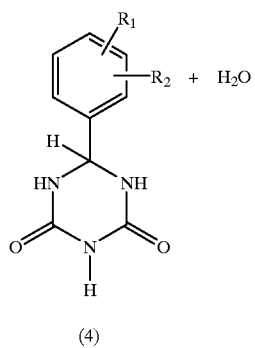

(4)

This method of preparation is another subject matter of this invention.

The compounds of formula (1) prepared according to the novel process are used as UV absorbers or are starting products for the preparation of UV absorbers.

With the novel process it is possible, for example, to prepare compounds of formula

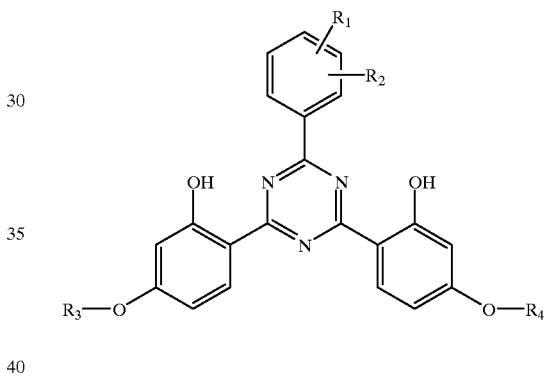

(7)

in simple manner and in good yields.

In formula (7):

R$_1$ and R$_2$ are each independently of the other hydrogen; hydroxy or C$_1$–C$_5$alkoxy;

R$_3$ and R$_4$ are each independently of the other C$_3$–C$_{18}$alkyl; C$_2$–C$_{18}$alkenyl; a radical of formula —CH$_2$—CH(—OH)—CH$_2$—O—T$_1$;

a radical of formula

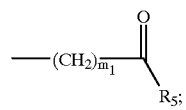

(7a)

R$_5$ is hydroxy; C$_1$–C$_5$alkoxy which is unsubstituted or substituted by one or more than one OH group; amino; mono- or di-C$_1$–C$_5$alkylamino; M; a radical of formula

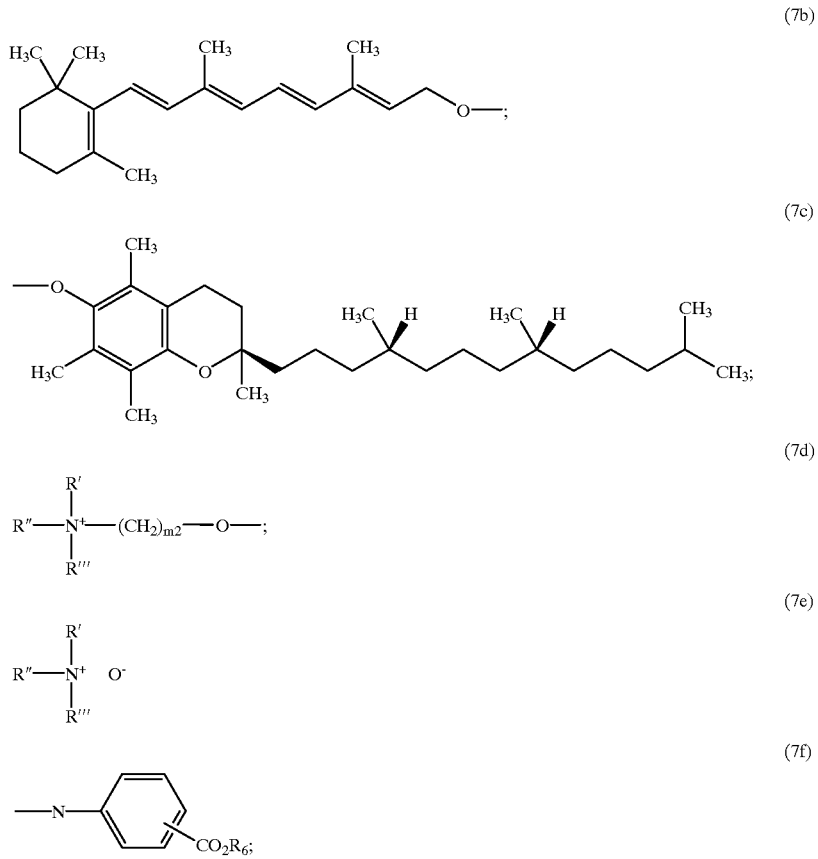

(7b)

(7c)

(7d)

(7e)

(7f)

wherein R', R" and R'" are each independently of one another $C_1$–$C_{14}$alkyl which is unsubstituted or substituted by one or more than one OH group;

$R_6$ is hydrogen; M; $C_1$–$C_5$alkyl; or a radical of formula —$(CH_2)_{m_3}$—O—$T_1$;

$T_1$ is hydrogen; or $C_1$–$C_8$alkyl;

M is alkali metal; and $m_1$, $m_2$ and $m_3$ are each independently of one another 1 to 4.

The two resorcinol groups

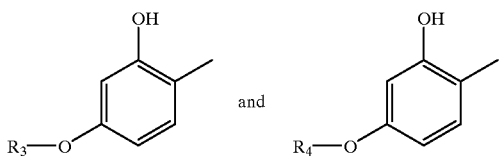

are introduced in generally known manner by Friedel-Crafts acylation of resorcinol in the presence of a Lewis acid, in particular aluminium chloride. In the last step, the etherification of the free hydroxyl groups in p-position is carried out, depending on the meaning of $R_3$ and $R_4$, by alkylation or acid-catalysed addition of glycidyl ethers.

The compounds of formula (7) are particularly suitable as UV filters, i.e. for protecting ultraviolet-sensitive organic materials, in particular skin and hair of humans and animals, from the harmful action of UV radiation. These compounds are therefore suitable as light stabilisers in cosmetic, pharmaceutical and veterinary preparations. These compounds can be used both in dissolved and in micronised state.

For use in cosmetics, these light stabilisers usually have an average particle size in the range from 0.02 to $2\mu$, preferably from 0.05 to $1.5\mu$ and, very particularly, from 0.1 to $1.0\mu$. The insoluble novel UV absorbers can be reduced to the desired particle size by customary methods, for example by grinding e.g. in a nozzle, ball, vibration or beater mill. Grinding is preferably carried out in the presence of 0.1 to 30% by weight, more preferably of 0.5 to 15% by weight, based on the UV absorber, of a grinding assistant such as an alkylated vinyl pyrrolidone polymer, a vinyl pyrrolidone/vinyl acetate copolymer, an acylglutamate or, in particular, a phospholipid.

In addition to the novel UV absorbers, the cosmetic formulation can also contain one or more than one further UV protective, for example an organic UV absorber from the class of the p-aminobenzoic acid derivatives, salicylic acid derivatives, benzophenone derivatives, dibenzoylmethane derivatives, diphenylacrylate derivatives, benzofuran derivatives, of the polymeric UV absorbers, containing one or several silicium-organic radicals, cinnamic acid derivatives, camphor derivatives, trianilino-s-triazine derivatives, phenylbenzimidazolesulfonic acid and the salts thereof, menthylanthranilates, benzotriazole derivatives, and/or an inorganic micropigment selected from aluminium oxide- or silicium oxide-coated $TiO_2$, zinc oxide or mica.

The cosmetic formulations comprise 0.1 to 15% by weight, preferably 0.5 to 10% by weight, based on the total weight of the formulation, of a UV absorber or of a mixture of UV absorbers and a cosmetically compatible auxiliary.

The cosmetic formulations can be prepared by physically mixing the UV absorber(s) with the auxiliary by conventional methods, such as by simply stirring the individual components together.

The cosmetic formulations can be formulated as water-in-oil or oil-in-water emulsion, as oil-in-alcohol lotion, as vesicular dispersion of a ionic or nonionic amphiphilic lipid, as gel, solid stick or as aerosol formulation.

As water-in-oil or oil-in-water emulsion, the cosmetically compatible auxiliary preferably comprises 5 to 50% of an oil phase, 5 to 20% of an emulsifier and 30 to 90% of water. The oil phase can in this case contain any oil suitable for cosmetic formulations, for example one or several hydrocarbon oils, wax, natural oil, silicone oil, fatty acid ester or fatty alcohol. Preferred mono- or polyols are ethanol, isopropanol, propylene glycol, hexylene glycol, glycerol and sorbitol.

To prepare the cosmetic formulations it is possible to use any conventionally usable emulsifier, typically one or several ethoxylated esters of natural derivatives, such as polyethoxylated esters of hydrogenated castor oil; or a silicone oil emulsifier, such as silicone polyol; a free or ethoxylated fatty acid soap; an ethoxylated fatty alcohol; a free or ethoxylated sorbitan ester; an ethoxylated fatty acid; or an ethoxylated glyceride.

The cosmetic formulations can also contain other components, for example emollients, emulsion stabilisers, skin moisturisers, suntan promoters, thickeners such as xanthan, moisture retention agents such as glycerol, preservatives, fragrances and colourants.

The cosmetic formulations are distinguished by excellent protection of the human skin against the harmful action of sunlight.

In the following Examples, percentages are by weight and the amounts relate to the pure substance.

EXAMPLE 1

Preparation of 4,6-dioxy-2-(4-methoxyphenyl)-1,2-dihydro-1,3,5-triazine

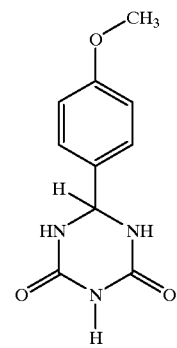

(101)

A ground glass flask is charged with 951 g of 37% hydrochloric acid and then 105.1 g of biuret are stirred in and 136.15 g (1 mol) of anisaldehyde are added at room temperature. This suspension is stirred for 18 hours. An additional 18.5 g of biuret and 95 g of 37% hydrochloric acid are added and the reaction mixture is stirred for 4 hours. The contents of the reactor are then added to 3000 ml of ice water and filtered through a suction filter. The filter cake is washed with a large amount of water and dried under vacuum.

Yield: 214 g of the compound of formula (101)

EXAMPLES 2 TO 6

The compounds of formulae (102) to (106) listed in Table 1 are obtained in analogy to Example 1.

TABLE 1

| Example | Aldehyde starting compound | Final compound |
|---|---|---|
| 2 | ![vanillin structure] | ![compound 102] (102) |
| 3 | ![salicylaldehyde structure] | ![compound 103] (103) |

TABLE 1-continued

| Example | Aldehyde starting compound | Final compound |
|---|---|---|
| 4 | | (104) |
| 5 | | (105) |
| 6 | | (106) |

What is claimed is:

1. A process for the preparation of an aryl-1,3-5-triazine compound of formula (1), which comprises reacting an aldehyde compound of formula (2) with biuret, compound of formula (3), in hydrochloric acid or with MeSO$_3$H (1$^{st}$ reaction step), then oxidising the resulting compound of formula (4) to the compound of formula (5) or (6) (2$^{nd}$ reaction step) and subsequently chlorinating the compound so obtained to the compound of formula (1) (3$^{rd}$ reaction step) according to the following scheme:

1st step:

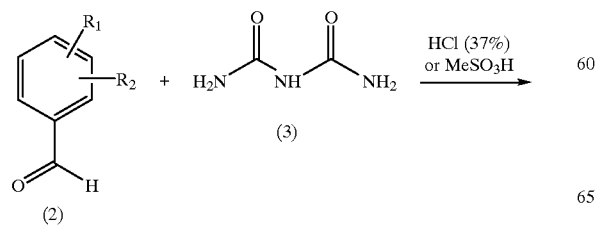

-continued

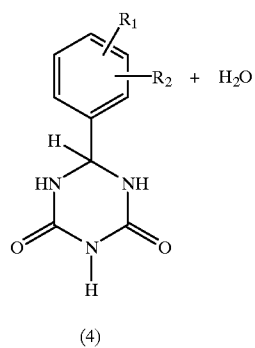

2nd step:

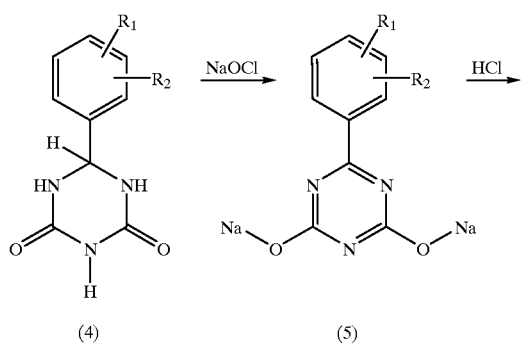

3rd step:

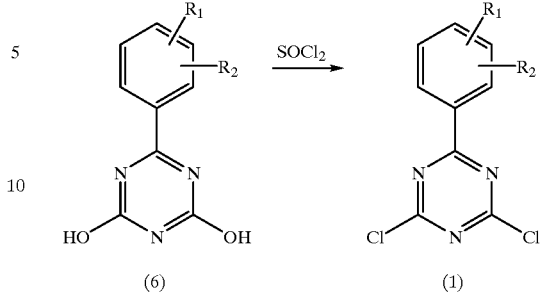

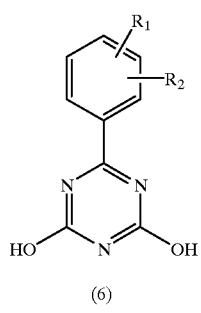

in which above scheme
R$_1$ and R$_2$ are each independently of the other hydrogen, hydroxy or C$_1$–C$_5$alkoxy.

2. A process according to claim 1, wherein the reaction time of the first reaction step is from 1 to 24 hours.

3. A process according to claim 1, wherein the first reaction step is carried out in the temperature range from 0 to 60° C.

4. A process according to claim 3, wherein the first reaction step is carried out at room temperature.

5. A process according to claim 1, wherein
R$_1$ is C$_1$–C$_5$alkoxy; and
R$_2$ is hydrogen.

6. A process according to claim 5, wherein
R$_1$ is methoxy.

* * * * *